(12) United States Patent
Newman et al.

(10) Patent No.: US 8,085,901 B2
(45) Date of Patent: *Dec. 27, 2011

(54) FIRING DELAY FOR RETROFIT DIGITAL X-RAY DETECTOR

(75) Inventors: Peter A. Newman, Pittsford, NY (US); Michael P. Urbon, Churchville, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/956,517

(22) Filed: Nov. 30, 2010

(65) Prior Publication Data

US 2011/0096908 A1    Apr. 28, 2011

Related U.S. Application Data

(63) Continuation of application No. 12/271,962, filed on Nov. 17, 2008, now Pat. No. 7,844,031.

(60) Provisional application No. 60/989,144, filed on Nov. 20, 2007, provisional application No. 60/989,151, filed on Nov. 20, 2007.

(51) Int. Cl.
*H05G 1/56* (2006.01)
(52) U.S. Cl. ......................................... 378/114; 378/116
(58) Field of Classification Search .................. 378/91, 378/98, 98.5, 98.8, 102, 114, 115, 116, 189, 378/210

See application file for complete search history.

(56) References Cited

U.S. PATENT DOCUMENTS

| 7,844,031 B2 * | 11/2010 | Newman et al. ............... 378/114 |
| 2006/0008054 A1 | 1/2006 | Ohara |
| 2007/0145280 A1 | 6/2007 | Campbell |

FOREIGN PATENT DOCUMENTS

| WO | WO01/33921 | 5/2001 |
| WO | WO2007/098920 | 9/2007 |

OTHER PUBLICATIONS

Anonymous, "CDRPan for Panoramic Systems, Instructions for Panoramic Corporation PC-1000," Oct. 2000, XP-002516607, Retrieved from the Internet: URL:http://www.schicktech.com/uploads/downloads/B1051101Rev-.pdf.

* cited by examiner

*Primary Examiner* — Hoon Song

(57) ABSTRACT

A method and apparatus are disclosed for obtaining an x-ray image from an x-ray imaging apparatus using a digital radiography receiver installs a retrofit connection apparatus that adapts the x-ray imaging apparatus for use with the digital radiography receiver by forming a receiver interface channel for communicating signals to and from the digital radiography receiver, forming an operator interface channel for routing at least an input expose signal from an operator control to the connection apparatus and forming a generator interface channel for transmitting at least an output expose signal from the retrofit connection apparatus to an x-ray generator of the x-ray imaging apparatus. An input expose signal over the operator interface channel initiates a reset of the digital radiography receiver over the receiver interface channel before the output expose signal to the x-ray generator is transmitted over the generator interface channel.

20 Claims, 19 Drawing Sheets

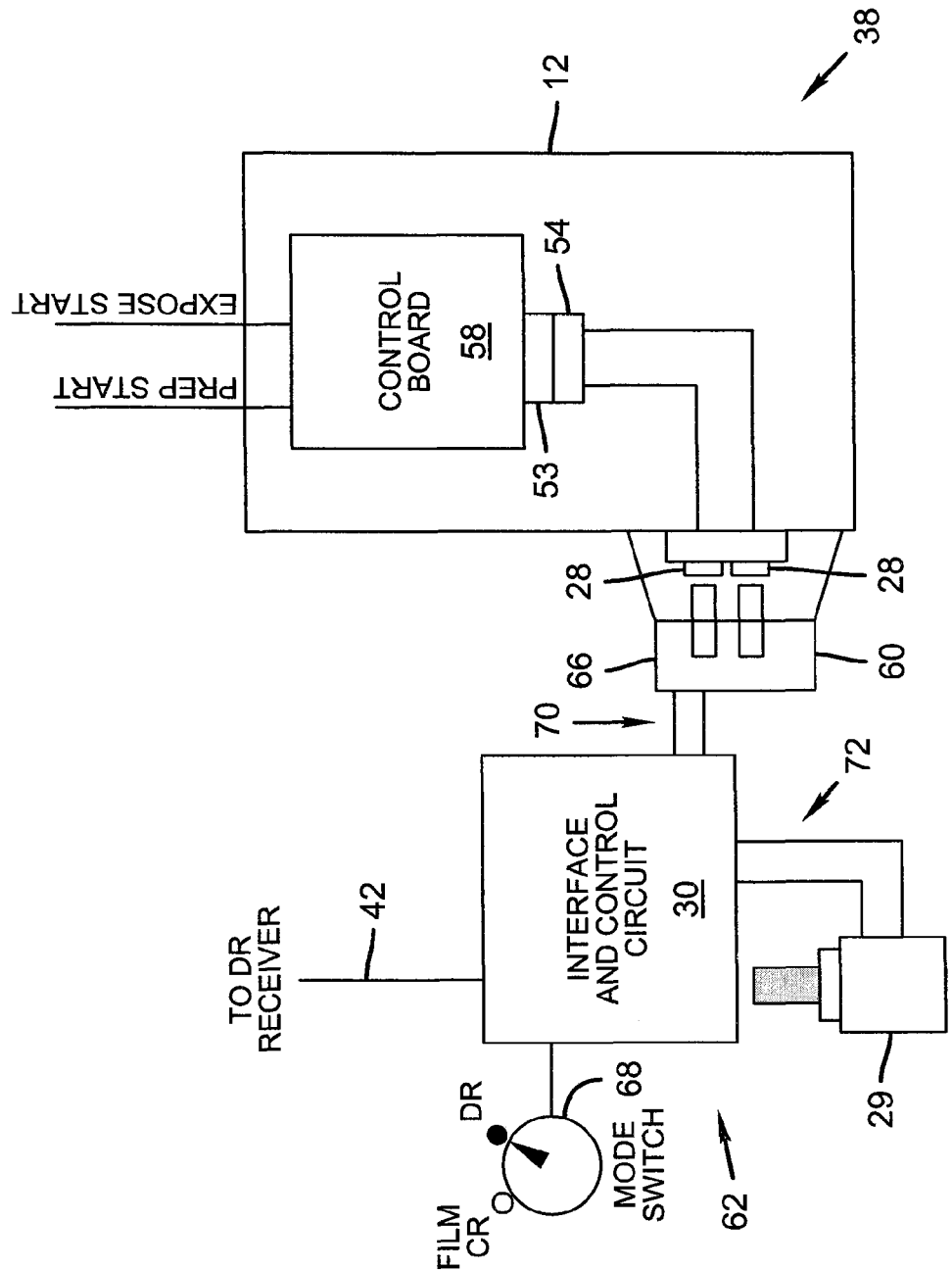

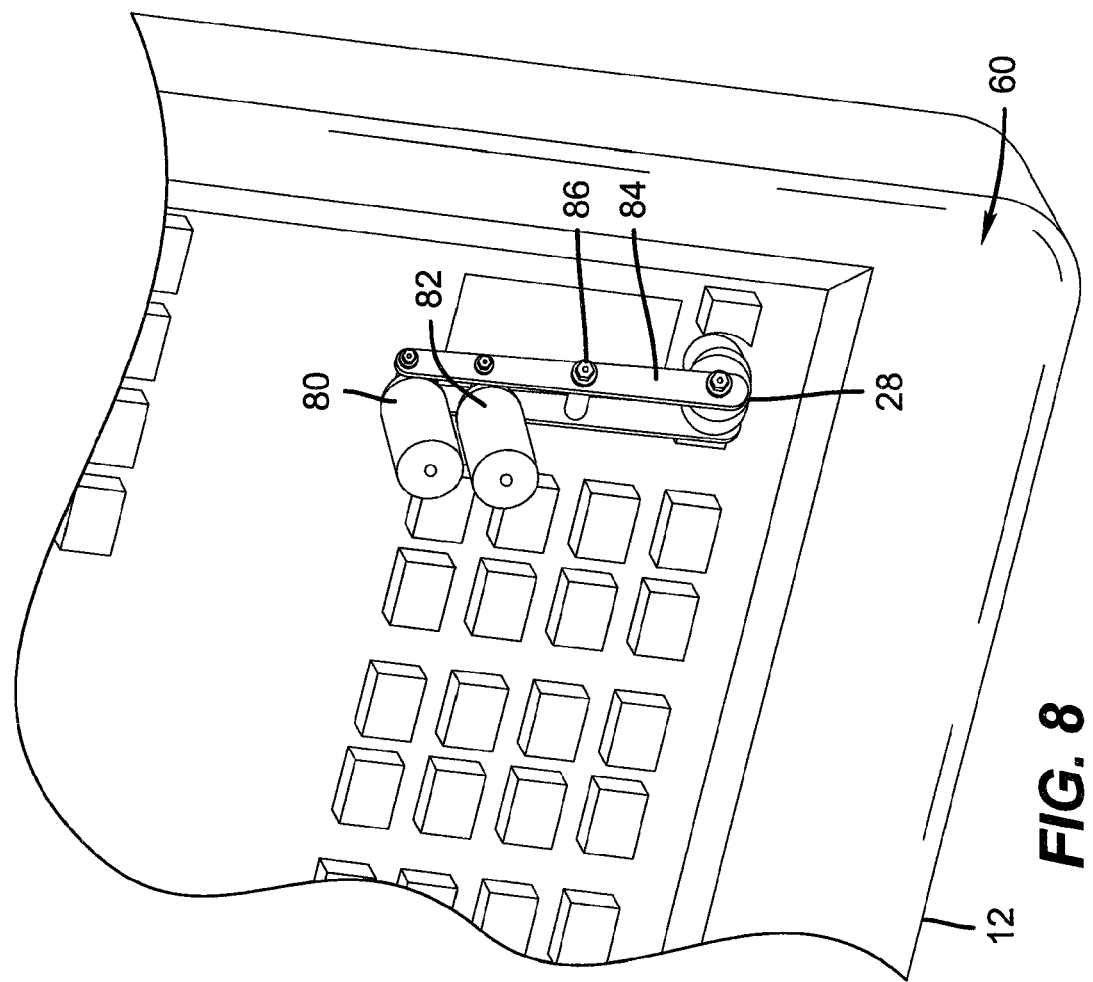

FIRING DELAY FOR RETROFIT DIGITAL X-RAY DETECTOR

CROSS REFERENCE TO RELATED APPLICATIONS

This application is a continuation of the following, U.S. patent applications, each of which is incorporated by reference into this specification:

Priority is claimed from commonly assigned, U.S. patent application Ser. No. 12/271,962, filed Nov. 17, 2008, now U.S. Pat. No. 7,844,031 entitled: FIRING DELAY ON X-RAY EXPOSURE TO PREPARE A RETROFIT DR DETECTOR FOR IMAGE ACQUISITION, in the name of Newman et al., provisional patent application Ser. Nos. (a) 60/989,144, filed Nov. 20, 2007, entitled "FIRING DELAY ON X-RAY EXPOSURE TO PREPARE A RETROFIT DR DETECTOR FOR IMAGE ACQUISITION", in the name of Newman; and (b) 60/989,151, filed Nov. 20, 2007, entitled "BUTTON PUSHING MECHANISM FOR A RETROFIT DR DETECTOR", in the name of Urbon, the disclosures of both of which are incorporated by reference.

FIELD OF THE INVENTION

The invention relates generally to digital x-ray imaging and more particularly relates to an apparatus and a method for adapting the timing sequence of a conventional film-based and/or computed radiography (CR) x-ray imaging system for using a retrofit digital radiography (DR) detector.

BACKGROUND OF THE INVENTION

DR is an alternative to x-ray imaging technologies that rely on photosensitive film layers to capture radiation exposure and thus to produce and store an image of a subject's internal physical features. With digital radiography, the radiation exposure energy captured on radiation sensitive layers of a digital x-ray detector is converted, pixel by pixel, to electronic image data which is then stored in memory circuitry for subsequent read-out and display on suitable electronic image display devices. One of the driving forces in the success of digital radiography is the ability to rapidly visualize and communicate stored images via data networks to one or more remote locations for analysis and diagnosis by the radiologist, without the delay that results when film must be developed and checked, then packaged and mailed or sent by courier to a remote location.

DR is viewed as having some advantages over conventional film-based and earlier computed radiography (CR) systems. For example, DR provides the ability to obtain radiographic image data without the need to move, handle, process, or scan any type of imaging medium following exposure. Data downloaded directly from the DR receiver panel is then available for viewing and diagnosis on-site or at any appropriately networked viewer workstation.

Improvements in performance, miniaturization, and packaging have enabled the development of a portable DR receiver panel that is battery-powered and capable of wireless communication for control signals and image data. Among other advantages, this provides a DR receiver panel having a low-profile design that can be compatible with receiver dimensions used for earlier film and CR systems.

While DR imaging systems have advantages over earlier film and CR systems, replacing such a earlier x-ray system can be very costly, thereby limiting the availability of DR systems as hospitals attempt to maximize their investment in older equipment and to extend its usable lifetime.

To meet the need for the improved capabilities offered by DR imaging, a number of companies that provide x-ray equipment offer retrofit configurations that allow a DR receiver panel to be used with existing x-ray components, in place of a film or CR cassette. Existing retrofit solutions, however, have one or more limitations, in that they:

(a) do not allow use of both earlier types of receivers and the newer DR panels. A retrofit that completely converts existing hardware to DR use but prevents the use of film or CR receivers is less desirable, since both film and CR media have particular strengths and may still be preferred in some types of imaging situations. There would be advantages to a retrofit solution that retains the ability to use the imaging system with film or CR receivers as well as allowing the use of DR receivers.

(b) do not minimize the impact of the retrofit on system hardware. Regulatory requirements for x-ray equipment make it highly undesirable to tamper with internal circuitry or connections, such as those required for a number of retrofit solutions. Invasive reconfiguration of an x-ray control panel could void existing approvals or certifications of the equipment or could even be in violation of regulatory rules and restrictions in some cases.

(c) do not minimize changes to workflow and impact upon patient care. A suitable retrofit solution should add the new capabilities of DR imaging with as little impact as possible on existing practices for positioning the patient and for obtaining exposures.

Thus, while various retrofit solutions have been proposed, there remains a need for a DR retrofit that has little or no impact on existing hardware, is minimally invasive with respect to the components of an existing x-ray system, and does not constrain the system's ability to use earlier film and CR imaging media.

SUMMARY OF THE INVENTION

An object of the present invention is to advance the art of diagnostic imaging. The invention provides a method and apparatus for retrofitting an existing film-based or CR x-ray imaging apparatus to capture an x-ray image using a DR receiver. A retrofit connection apparatus is provided that adapts the x-ray imaging apparatus for use with a DR receiver. The apparatus provides a receiver interface channel for communicating signals to and from the digital radiography receiver, an operator interface channel for routing at least an input expose signal from an operator control to the retrofit connection apparatus, and a generator interface channel for transmitting at least an output expose signal to an x-ray generator. The apparatus responds to the input expose signal over the operator interface channel by initiating a reset of the digital radiography receiver over the receiver interface channel before transmitting the output expose signal to the x-ray generator over the generator interface channel.

Another object of the present invention is to provide a retrofit solution that is substantially non-invasive, reducing or eliminating the likelihood that inspection or re-certification of equipment by regulatory authorities would be required.

Another object of the present invention is to provide a retrofit solution that allows an x-ray system user to use one or more earlier imaging media types in addition to the newer DR receiver panels.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

There is provided a method for obtaining an image by using a digital radiography receiver in an x-ray imaging system of a type configured for film or computed radiography. The method comprises: providing a retrofit connection apparatus that adapts the x-ray imaging system for use with the digital radiography receiver by: (a) forming a receiver interface channel for communicating signals to and from the digital radiography receiver; (b) forming an operator interface channel for routing at least an input expose signal from an operator control to the retrofit connection apparatus; and (c) forming a generator interface channel for transmitting at least an output expose signal from the retrofit connection apparatus to an x-ray generator of the x-ray imaging system; in response to the input expose signal routed over the operator interface channel, initiating a reset of the digital radiography receiver over the receiver interface channel; and transmitting the output expose signal to the x-ray generator over the generator interface channel.

There is provided an apparatus for x-ray imaging. The apparatus comprises an interface component installed as a retrofit to an x-ray imaging system. The interface component comprises: a mode selector for selecting at least a first mode setting for image capture using a digital radiography receiver and a second mode setting for image capture using a removable film or computed radiography cassette; a receiver interface channel for communication with such a digital radiography receiver, a generator interface channel for communication with an x-ray generator of such a system; an operator interface channel for communication with an operator control for receiving at least a first, preparation signal and a second, expose signal from an operator; and a programmed control logic processor that, when the first mode setting is selected, responds to such a second, expose signal from the operator interface channel by initiating a reset of such a digital radiography receiver over the receiver interface channel before transmitting an exposure signal to an x-ray generator of such a system over the generator interface channel.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 5E is a schematic block diagram of an embodiment of a retrofit connection apparatus that mounts a separate switch controller on the operator control console.

FIG. 8 is a perspective view of the inner components of the pushbutton control apparatus and shows their relation to the surface of the operator control console.

DETAILED DESCRIPTION OF THE INVENTION

Figure 1A:
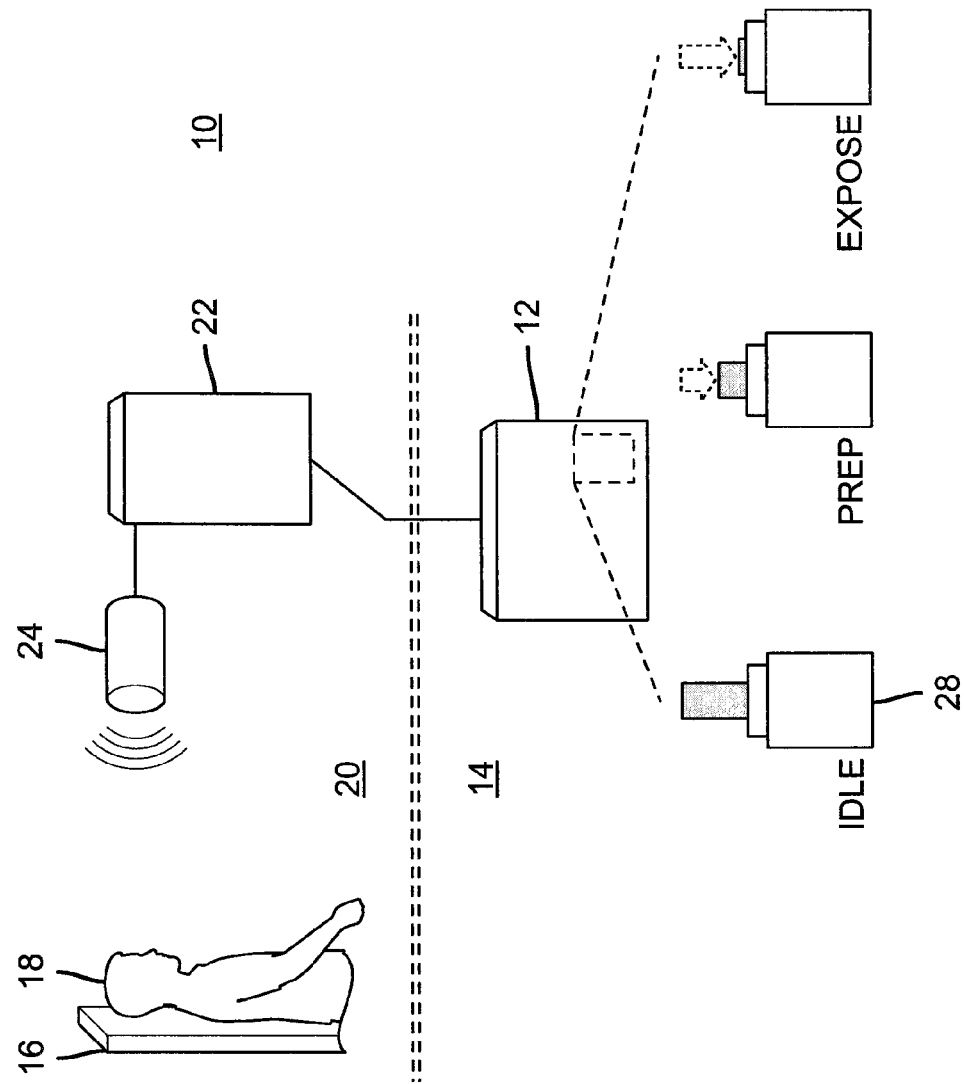
FIG. 1A is a schematic diagram showing a conventional x-ray imaging system.

The following is a detailed description of the preferred embodiments of the invention, reference being made to the drawings in which the same reference numerals identify the same elements of structure in each of the several figures.

FIG. 1A shows a conventional x-ray imaging system 10 that provides images on a removable medium, such as a removable film or CR cassette 16. An operator control console 12 is situated in a control room 14, shown below the dashed line in FIG. 1A and subsequent figures. An x-ray generator 22 is installed in a radiation room 20, shown above the dashed line. Cassette 16 is placed behind a patient 18 for obtaining the image. Exposure energy is provided by an x-ray tube 24 controlled from x-ray generator 22. Not shown, but widely used with conventional equipment are also exposure control apparatus, such as Automatic Exposure Control (AEC) devices that measure exposure levels and terminate exposure when a target radiation level has been received.

Figure 1B:
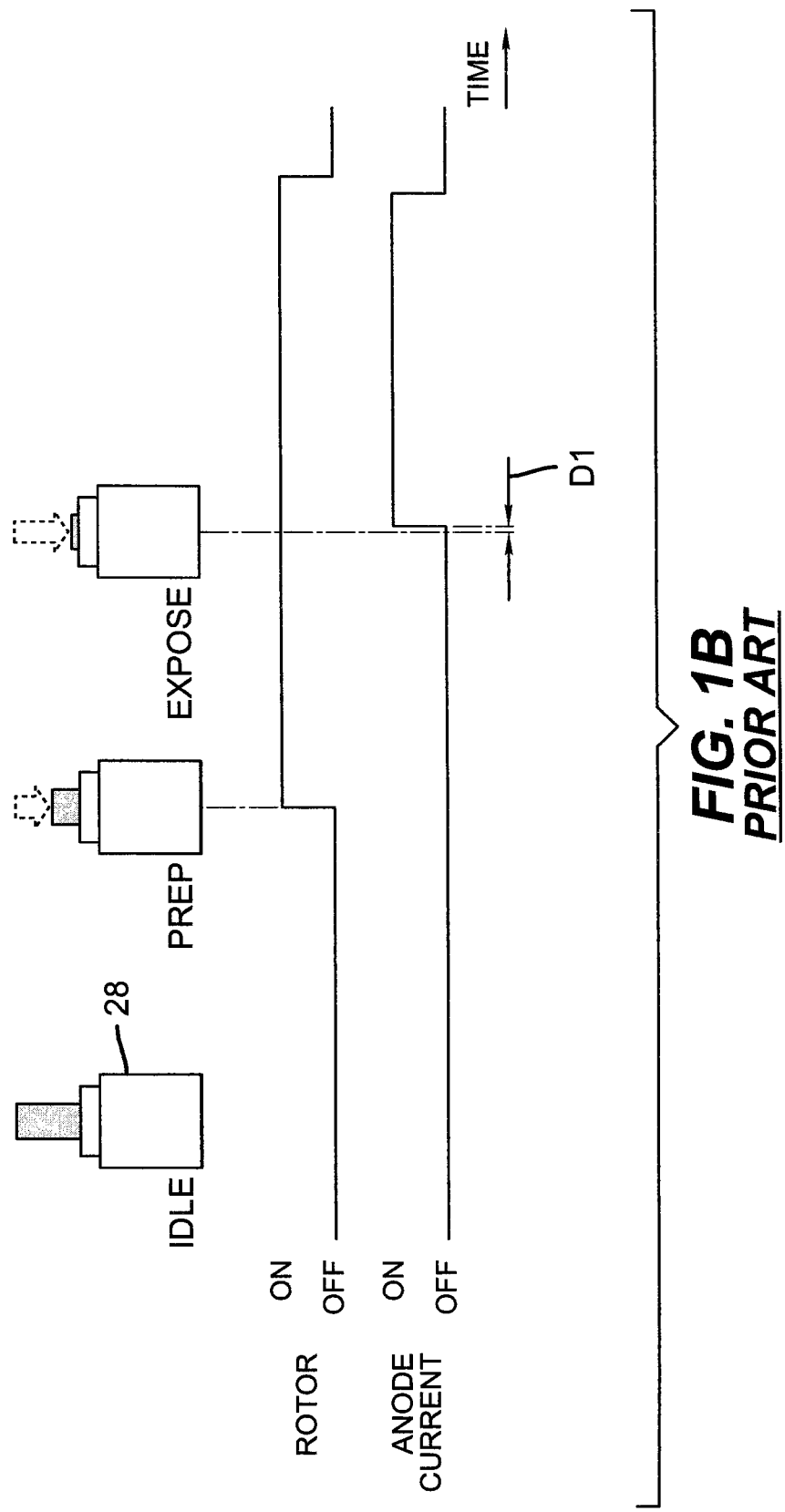
FIG. 1B shows timing states for using a conventional x-ray imaging system with removable film or CR media.

Referring to FIG. 1A and to the timing diagram of FIG. 1B, an operator control switch 28 that is operatively connected to, and operates as a part of, operator console 12 can be in any of three states, as controlled by the x-ray technician. Prior to patient set-up and imaging, the system is in an Idle state. Once the patient is properly positioned for imaging, with cassette 16 in place, the operator pushes switch 28 to advance to a Prep state. This instructs the x-ray system to ready itself for an upcoming exposure. In most systems, pressing the Prep switch, or otherwise entering a command to enter the Prep state, brings the rotor of x-ray tube 24 up to speed as a preparatory step. The operator may set and hold the Prep state, for example, while waiting for the patient to relax or to get into the best position for imaging. The Prep state itself can last from a few seconds to more than a minute in some cases.

When the Prep state is complete, an exposure can be taken as soon as the operator advances switch 28 to an Expose state or position.

In this sequence, once conditions are suitable for imaging, the operator advances the switch 28 setting to the Expose state. There is a momentary delay period D1, typically not more than about 1 millisecond, for response of the x-ray generator control circuitry. Current then goes to the anode of x-ray tube 24, which emits the ionizing radiation needed for exposure. At the conclusion of exposure, such as following a preset exposure time or when signalled by an AEC device or other exposure sensing device as described earlier, both rotor and anode current are de-energized and the Idle state resumes.

As is known to x-ray imaging practitioners, a number of additional conditions must also be satisfied to allow the flow of anode current to the x-ray tube. This includes, for example, requirements that equipment interlock conditions be satisfied and that rotor conditions be acceptable.

With different x-ray systems, switch 28 is variously embodied in one of a number of ways. In some systems, switch 28 is a two-position pushbutton mounted on operator console 12. In other systems, switch 28 is embodied as a bank of two pushbuttons or other controls on or near operator console 12, or as a tethered handswitch with a two-position pushbutton switch, connected by a cord that allows freer operator movement.

To provide a retrofit that allows use of a DR receiver panel as the x-ray detector in place of removable cassette 16 of the conventional system of FIG. 1A, the timing of the Prep and Expose states must change accordingly. In order to properly condition its sensing components for obtaining an exposure image, a DR receiver panel requires at least one reset cycle. Reset clears any residual noise, such as so-called "dark noise" from the pixels of the DR receiver panel so that the next exposure signal that is received is properly read. Only after reset is confirmed should the exposure energy be provided. It is also advantageous to time the exposure integration of the panel so that it follows close upon reset, rather than being further delayed.

Figure 2:
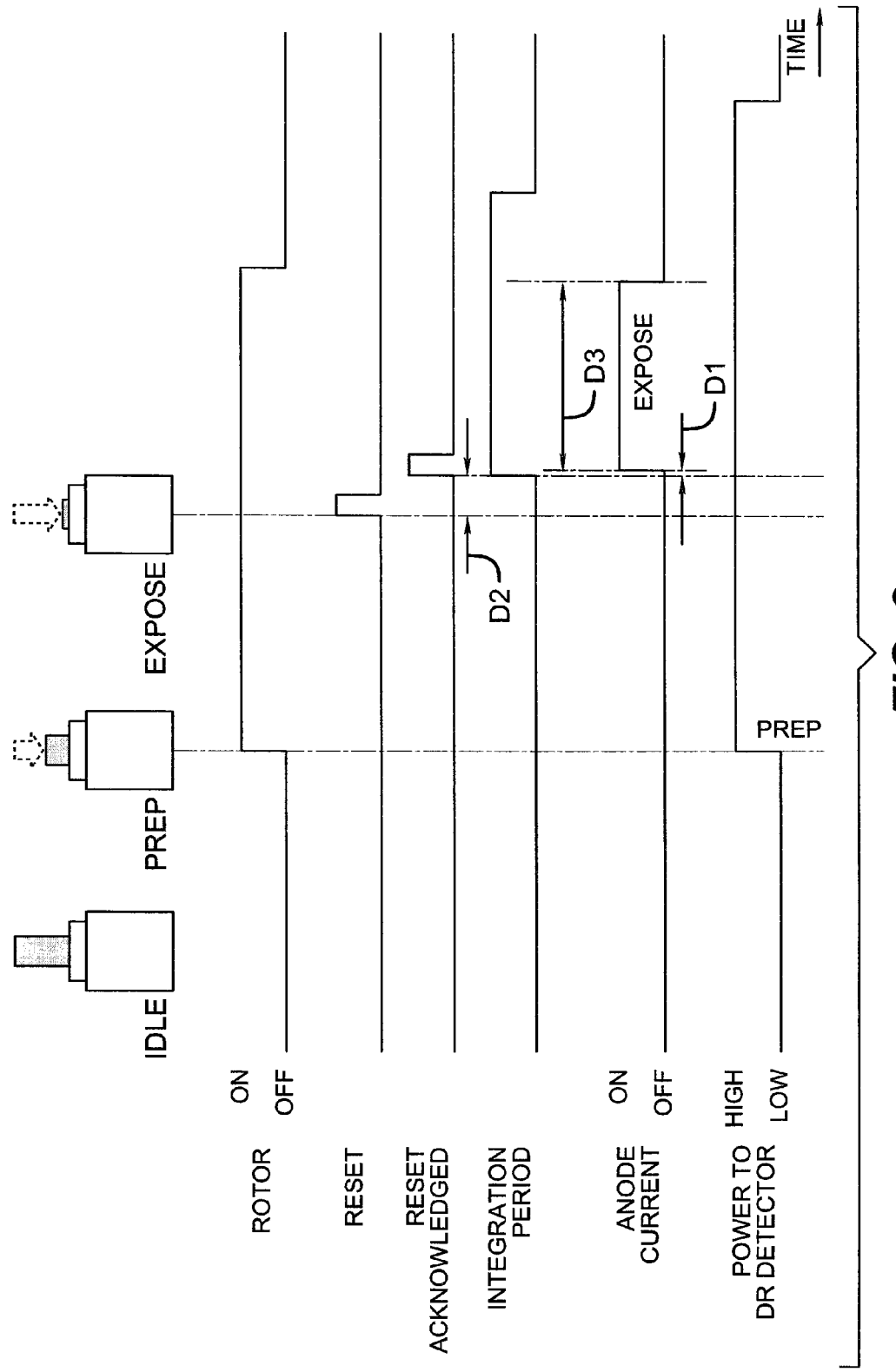
FIG. 2 shows timing states for using a digital radiography detector.

The timing diagram of FIG. 2 shows the sequence of Prep and Expose signals and related operations according to one DR retrofit embodiment of the present invention. As was shown for the conventional timing in FIG. 1B, pressing the Prep switch initiates x-ray tube rotor spin-up. In addition, this may also change the power mode of the DR receiver panel, particularly for a wireless, battery-powered DR detector. In the embodiment of FIG. 2, pressing the Prep switch sets DR receiver panel power from a low or standby level to a high level. During the period between pressing the Prep switch and pressing the Expose switch, normally from about 2-15 seconds, the operator typically observes the patient to assure that the patient remains still during exposure.

Pressing the Expose switch sends a reset signal to the DR receiver panel. Reset of DR detector image-sensing circuitry typically takes no more than about 300 milliseconds, shown as time period D2 in FIG. 2. An optional acknowledgement signal is received from the DR receiver panel when reset has been completed. In one embodiment, the reset acknowledgement is required in order for x-rays to be generated and anode current is not provided until a positive acknowledgement of reset has been received back from the DR receiver panel. This helps to prevent exposing the patient to the x-ray radiation when the DR panel is not ready to form an image. Anode current that drives x-ray generation is provided for a period D3 that is usually no more than about 500 milliseconds. The integration period of the DR receiver panel is typically about 1 second and begins just before anode current is provided, extending past the time when anode current is stopped. In FIG. 2, period D1 is again caused by x-ray generator control circuitry and represents the timing interval between the time integration begins at the DR receiver panel and the time x-rays are emitted (anode current ON).

It is noted that the timing diagram of FIG. 2 is exemplary and admits a number of modifications within the scope of the present invention. For example, the reset signal could alternately be provided from the moment the Prep switch is depressed, so that exposure and integration can begin more quickly following depressing the exposure switch. Delay time periods D1, D2, and D3 can vary in duration from those described. Timing, rather than positive reset acknowledgement, may be used to delay exposure (that is, with respect to FIG. 2, to delay anode current ON) for a brief period following selection by the operator in order to allow an interval for DR receiver panel reset before continuing. However, as noted earlier, requiring an actual acknowledgement of reset from the DR receiver panel itself may be more advantageous and may help to prevent wasted exposures where there is an equipment problem or communication difficulty.

As can be appreciated by comparing the timing diagram of FIG. 2 with the conventional timing shown in FIG. 1B, the retrofit task for using a DR receiver panel with an existing film or CR media system has an added measure of complexity: changing the timing sequence to allow sufficient delay for reset of the DR receiver panel sensing circuitry and timing the integration period of the DR receiver panel circuitry to just overlap the period during which x-rays are generated. Implementing this change also requires communication with the DR panel, both to initiate reset operation and, optionally, to receive confirmation that reset has been completed. As noted earlier in the background section, modifications to existing equipment are preferably not invasive, such as requiring that an existing x-ray operator control console have parts replaced or be rewired internally. As yet another complication, it would be considered disadvantageous to disable the existing operation scheme so that only the DR receiver panel could be used once the retrofit is installed and film or CR media were thus rendered unusable. It would be much more favorable to allow selectable use of either removable media, that is, either film or CR cassettes, or the DR receiver panel.

Figure 3:
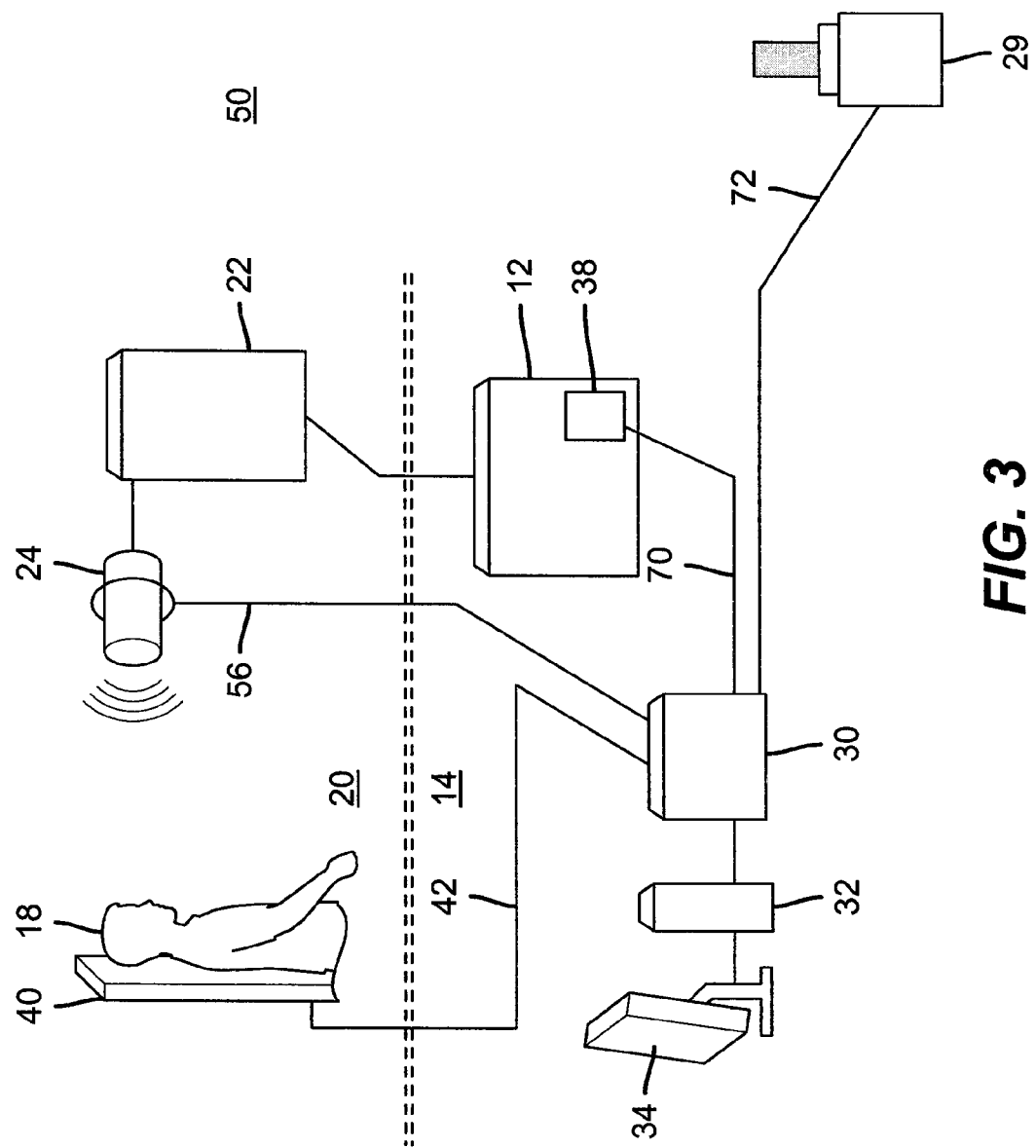
FIG. 3 is a schematic diagram showing an x-ray imaging system that has been retrofit according to one embodiment of the present invention.

The schematic diagram of FIG. 3 shows a retrofit imaging system 50 that substitutes a DR receiver panel 40 in place of cassette 16 and makes the necessary changes to x-ray exposure timing according to one embodiment of the present invention using wired connections. An interface and control circuit 30 communicates between DR receiver panel 40 and other components of this system. Image data itself goes to an imaging processor 32, such as a computer or workstation that is in communication with a display 34. A generator interface channel 70 connects interface and control circuit 30 to operator control console 12 by means of a connection apparatus 38 for providing Prep and Expose signals with the appropriate timing. An operator control switch 29 is connected to interface and control circuit 30 by an operator interface channel 72 for operator control, in place of switch 28 used in the conventional system of FIG. 1A. Switch 29 may be a tethered switch as in FIG. 3 or may be configured to mechanically control existing switches mounted on control console 12. A DR receiver interface channel 42 is provided between DR receiver panel 40 and interface an control circuit 30 by an ethernet cable connection or other type of high-speed data transfer link and may include other control signal lines for sending and receiving reset information and commands.

Figure 4:
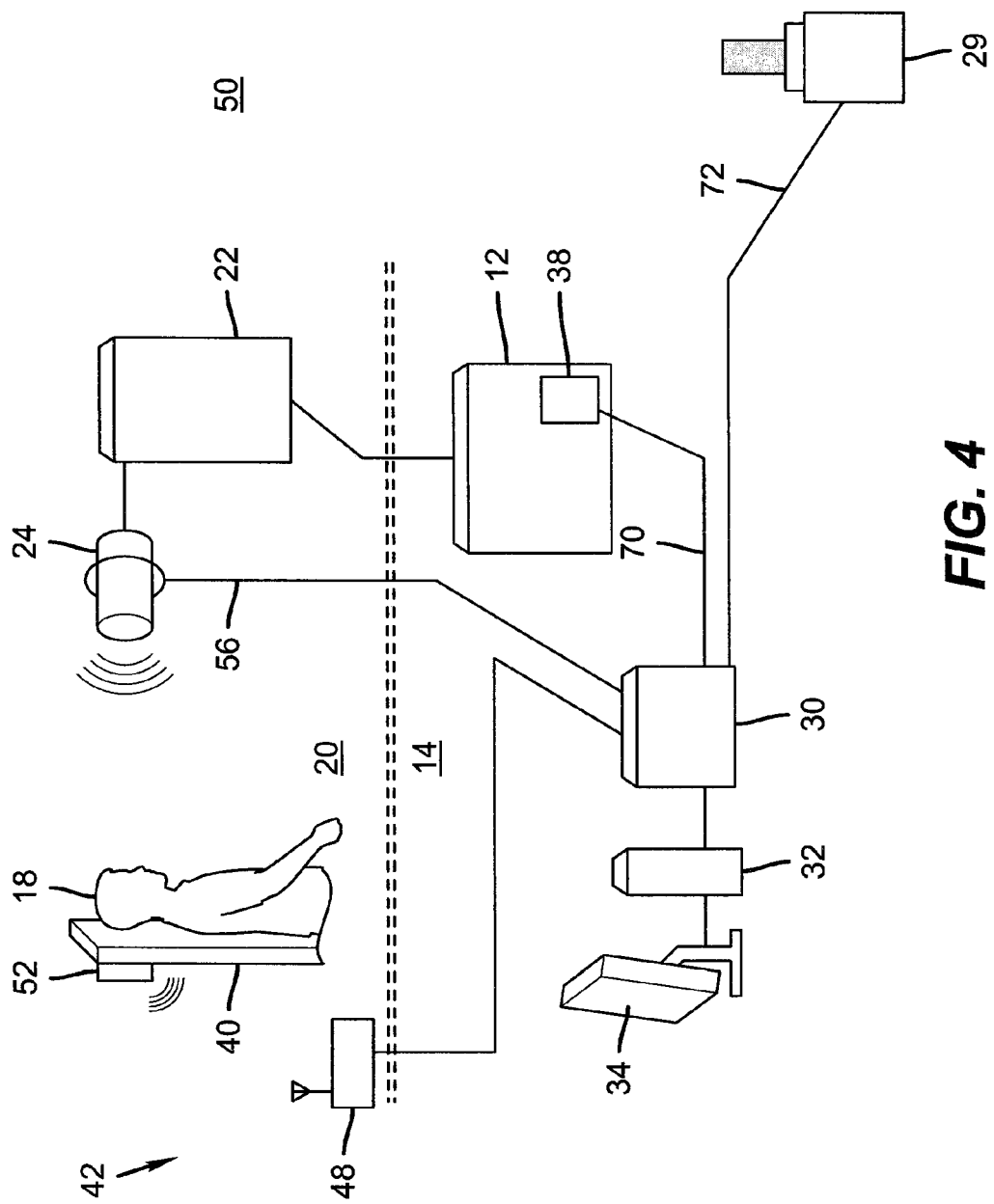
FIG. 4 is a schematic diagram showing a retrofit imaging system that has been retrofit according to a wireless embodiment of the present invention.

The schematic diagram of FIG. 4 shows retrofit imaging system 50 in an alternate, un-tethered embodiment. Here, a wireless communications link is provided for receiver interface channel 42 between DR receiver panel 40 and interface and control circuit 30. A transceiver 52 is connected to or provided as part of DR receiver panel 40 and communicates with a transceiver 48 that is connected to or provided as part of interface and control circuit 30. In one embodiment, battery power is also provided within DR receiver panel 40, so that no external wiring is required to the panel for operation. In another embodiment, only a power cord connection to DR receiver panel 40 is needed; the transmission channel to interface and control circuit 30 is wireless.

FIGS. 3 and 4 also show an optional sensor 56 for detecting a level of anode current that indicates active x-ray emission from x-ray tube 24. Anode current sensing by sensor 56 can be used to indicate that signal integration at DR receiver panel 12 should be terminated. It should be observed that the use of this additional sensor can also be done in a non-invasive manner and may therefore be preferable to other methods such as detecting or interrupting a termination signal from an AEC device, as described earlier, for example.

Figure 5A:
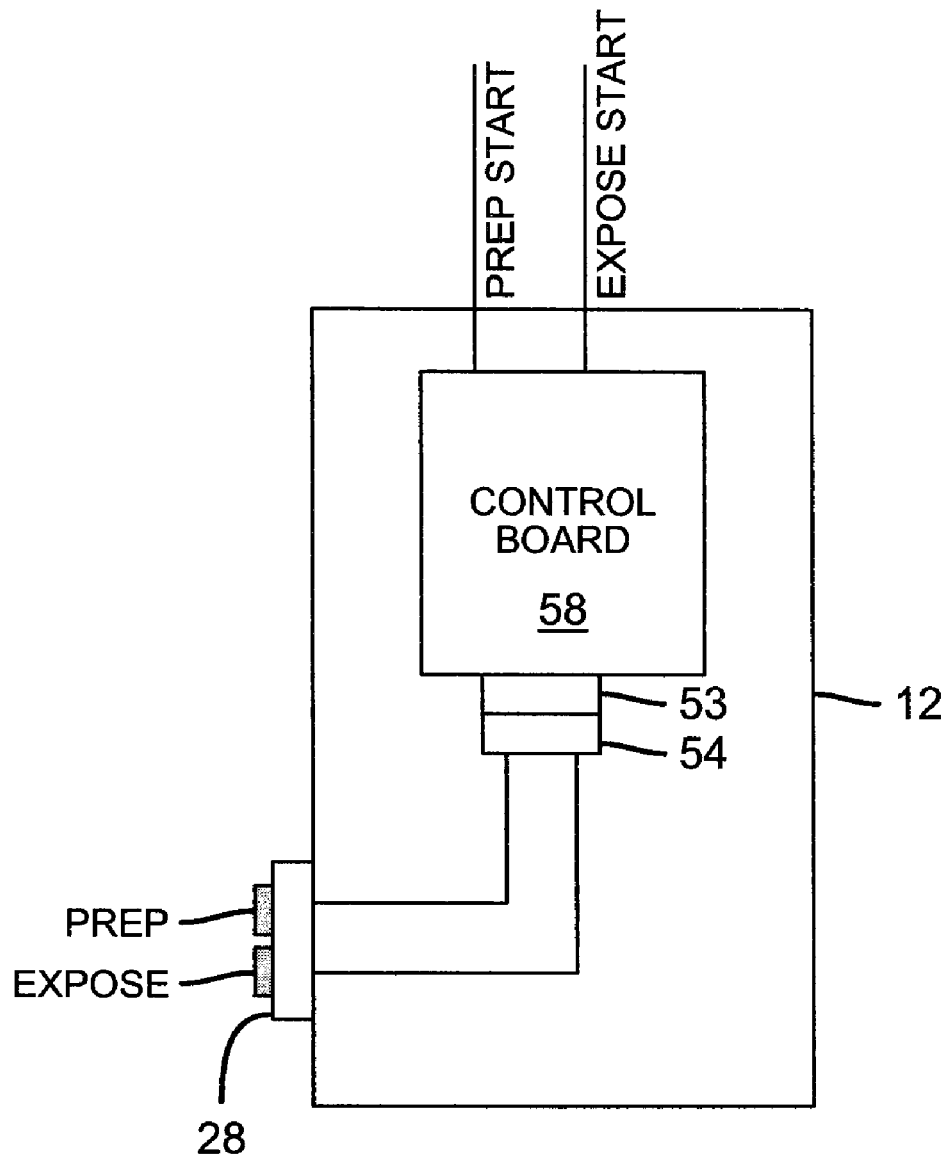
FIG. 5A is a schematic block diagram of a conventional operator control console, such as used in the system of FIG. 1.

The schematic block diagram of FIG. 5A shows how switch 28 conventionally has been connected to provide Prep and Expose signals in operator control console 12. A control board 58 within operator control console 12 accepts signals from switch 28 by means of a connector 54 that mates with a connector 53 that is in communication with control board 58. Switch 28 can be provided by a single two-position switch as already discussed, with one position for the Prep signal, the other for the Expose signal; or by multiple switch elements, one switch element for the Prep signal, the other for the Expose signal, as illustrated in FIG. 5A. Switch 28 may be panel-mounted or tethered, as described earlier. The schematic block diagrams of FIGS. 5B, 5C, 5D, 5E, and 5F then show how the conventional arrangement of operator control console 12 connections is changed in different embodiments of connector apparatus 38.

Figure 5B:
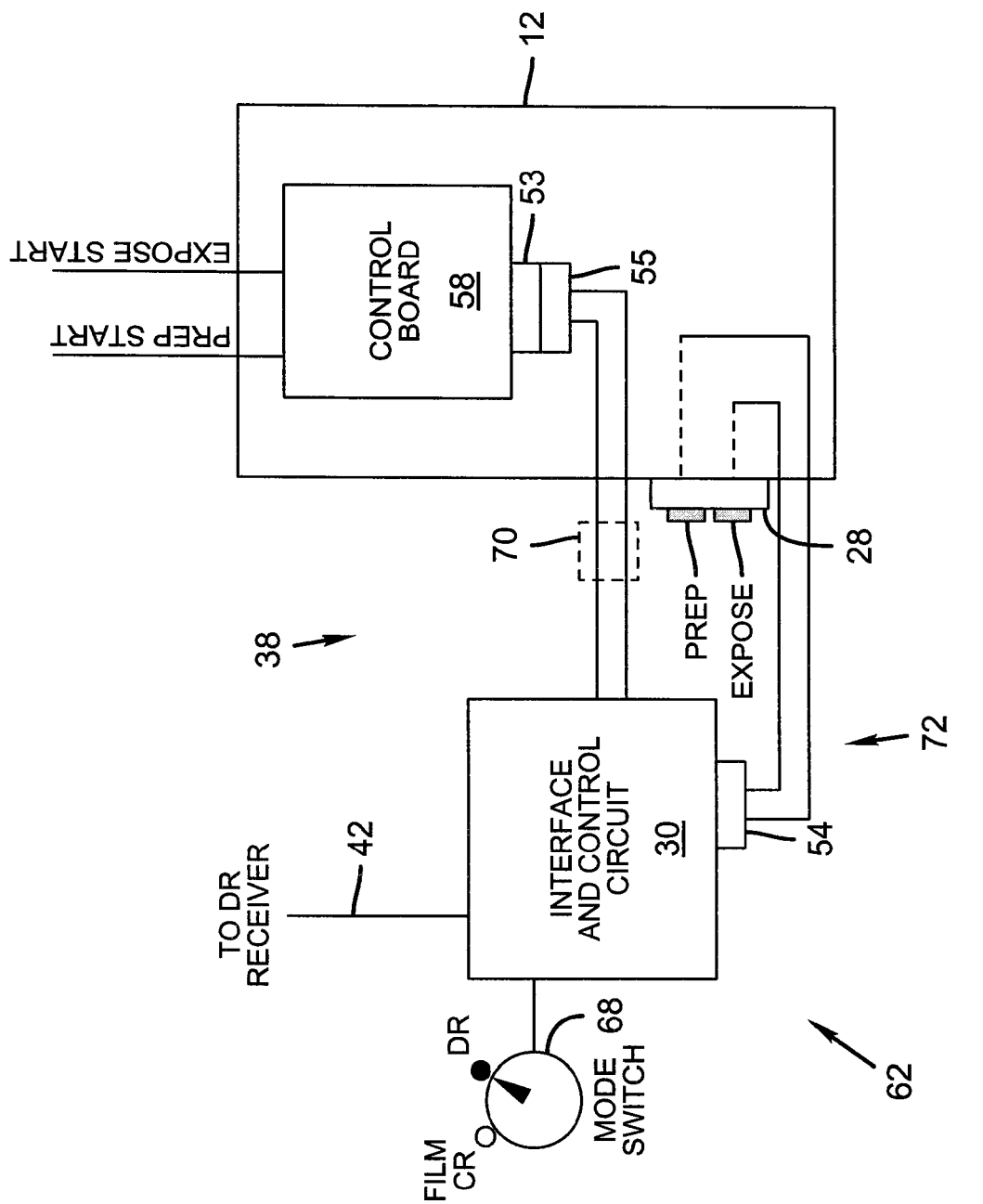
FIG. 5B is a schematic block diagram of an embodiment of a retrofit connection apparatus that uses panel-mounted or tethered switches of the existing imaging apparatus.

Referring to one embodiment of a retrofit apparatus 62 in FIG. 5B, switch 28 of the original system is used with the retrofit connection of connector apparatus 38. Connector 54 is removed from connector 53 on control board 58 and re-connected to interface and control circuit 30 to form operator interface channel 72. Interface and control circuit 30 then uses timing as discussed with regard to FIG. 2 and conditions the signals from switch 28 on operator interface channel 72 to provide the needed delay and provides the conditioned signals over generator interface channel 70 at a connector 55 to control board 58. Switch 28 in such an embodiment may be panel-mounted or tethered. In one embodiment, connector 53 is externally mounted as a jack or plug for tethered switch 28 connection, making it particularly straightforward to provide the retrofit arrangement of connection apparatus 38.

Still referring to FIG. 5B, an optional mode selector 68 is provided for interface control circuit 30 in one embodiment. Mode selector 68 can be used to specify operation of control logic in interface and control circuit 30, in order to enable either the signal timing of a first mode shown in FIG. 1A when removable media (film or CR cassette) is used or the signal timing of a second mode shown in FIG. 2 when a DR receiver panel is used. Other types of mode selector can be provided, including a programmed or operator-entered computer instruction that specifies either mode, entered from a touchscreen, keyboard, keypad, or mouse or other type of pointer, for example. Using a mode selector switch or other mode selection mechanism, the same x-ray imaging apparatus can provide imaging on either removable media or the DR digital receiver panel, allowing the operator to choose the imaging mode of preference.

Figure 5C:
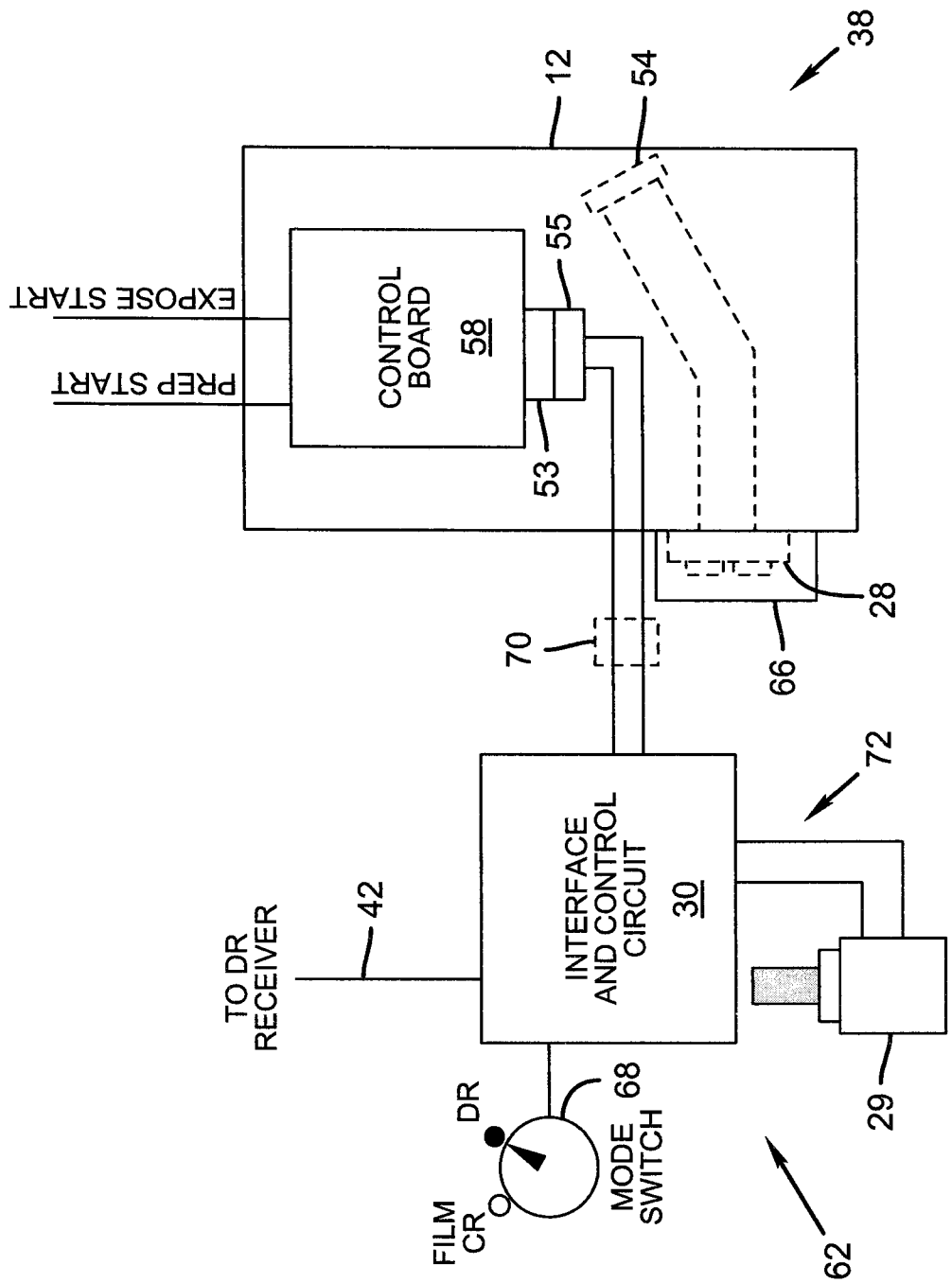
FIG. 5C is a schematic block diagram of an embodiment of a retrofit connection apparatus that uses a separate external switch and disables the existing switch for Prep and Expose functions of the apparatus of FIG. 5B.

Referring to the alternate embodiment of retrofit apparatus 62 shown in FIG. 5C, existing switch or switches 28 are not used with the retrofit arrangement of connection apparatus 38. Here, connector 54 is disconnected from control board 58 or otherwise bypassed, and a cover 66 is applied over switches 28, preventing these switches from being seen and used. Tethered switch 29 on operator interface channel 72 substitutes as the switch for sending Prep and Expose signals to interface and control circuit 30. Connection is provided over generator interface channel 70 from interface and control circuit 30 to inner control board 58.

Figure 5D:
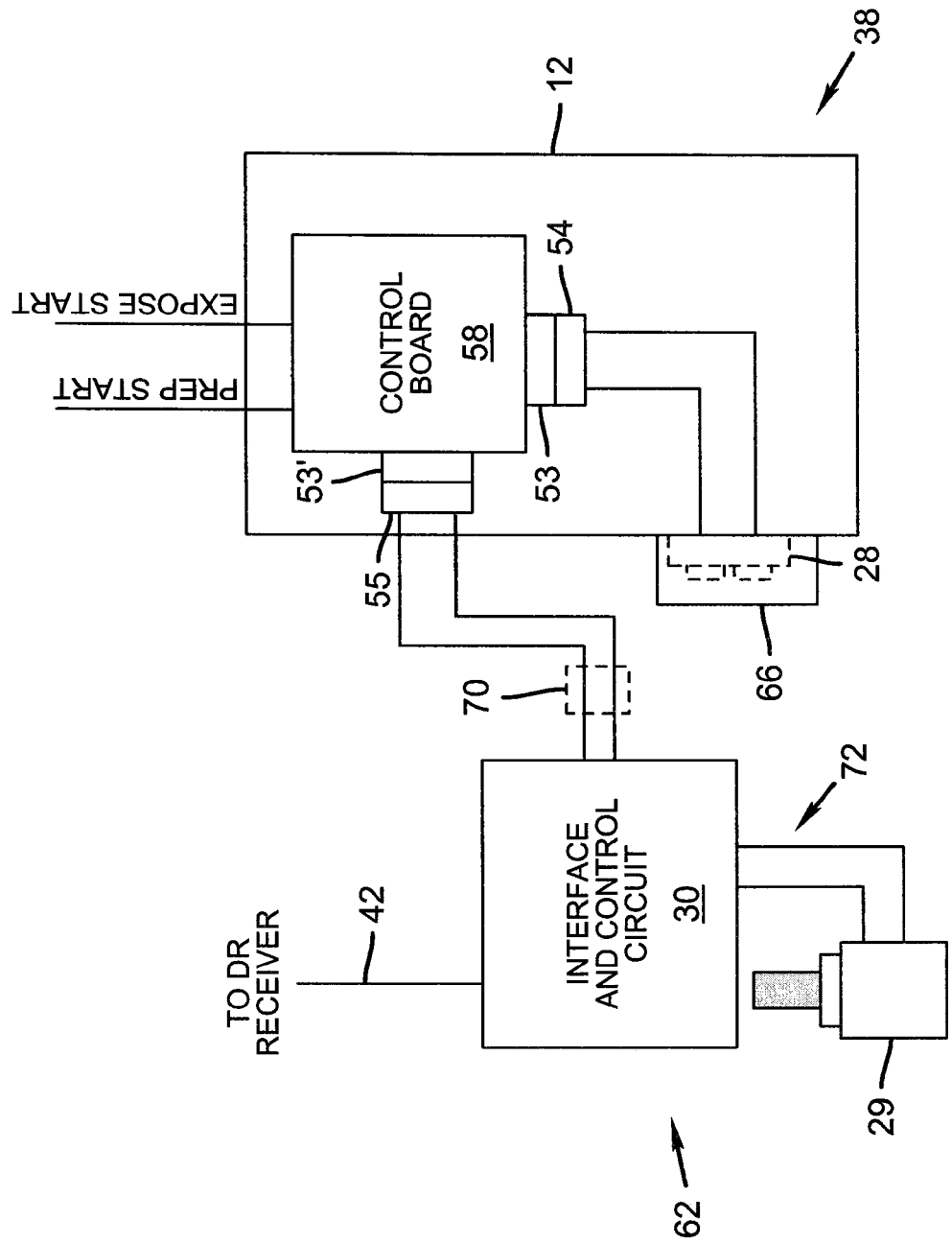
FIG. 5D is a schematic block diagram of an alternate embodiment for a retrofit connection apparatus that has connection to both existing and retrofit Prep and Expose switches.

The schematic block diagram of FIG. 5D shows an alternate embodiment of retrofit apparatus 62 in which mode selector 68 would not be necessary, since both switches 28 and 29 are connected. In this embodiment, generator interface channel 70 connects to control board 58 at a second connector 53'. Cover 66 is removable or has an access door or panel, allowing the technician to obtain images from removable film or CR media using switch 28 when exposed; for DR receiver panel imaging, the technician uses switch 29.

Yet another alternate embodiment of retrofit apparatus 62 is shown in FIG. 5E. This embodiment of connector apparatus 38 mounts a switch controller 60 over a pair of switches 28. Switch controller 60 mechanically manipulates each of switches 28 for sending Prep and Expose signals, respectively, to control board 58. The operator uses one or two switches 29 to send Prep and Expose signals. Switches 29 can be separately mounted or tethered, or can be mounted on switch controller 60. No internal re-wiring is needed with this embodiment; switch controller 60 includes an appropriate type of actuator, such as one or more solenoids, for example, selectively energized in order to operate existing switches 28 under control of interface and control circuit 30 with this embodiment. Generator interface channel 70 is thus used to manipulate existing pushbutton switches in this embodiment. In one embodiment, cover 66 can be removed for use when it is desirable to obtain an image on a removable film or CR cassette, using switches 28 rather than using the DR receiver panel using one or two switches 29.

Figure 5F:
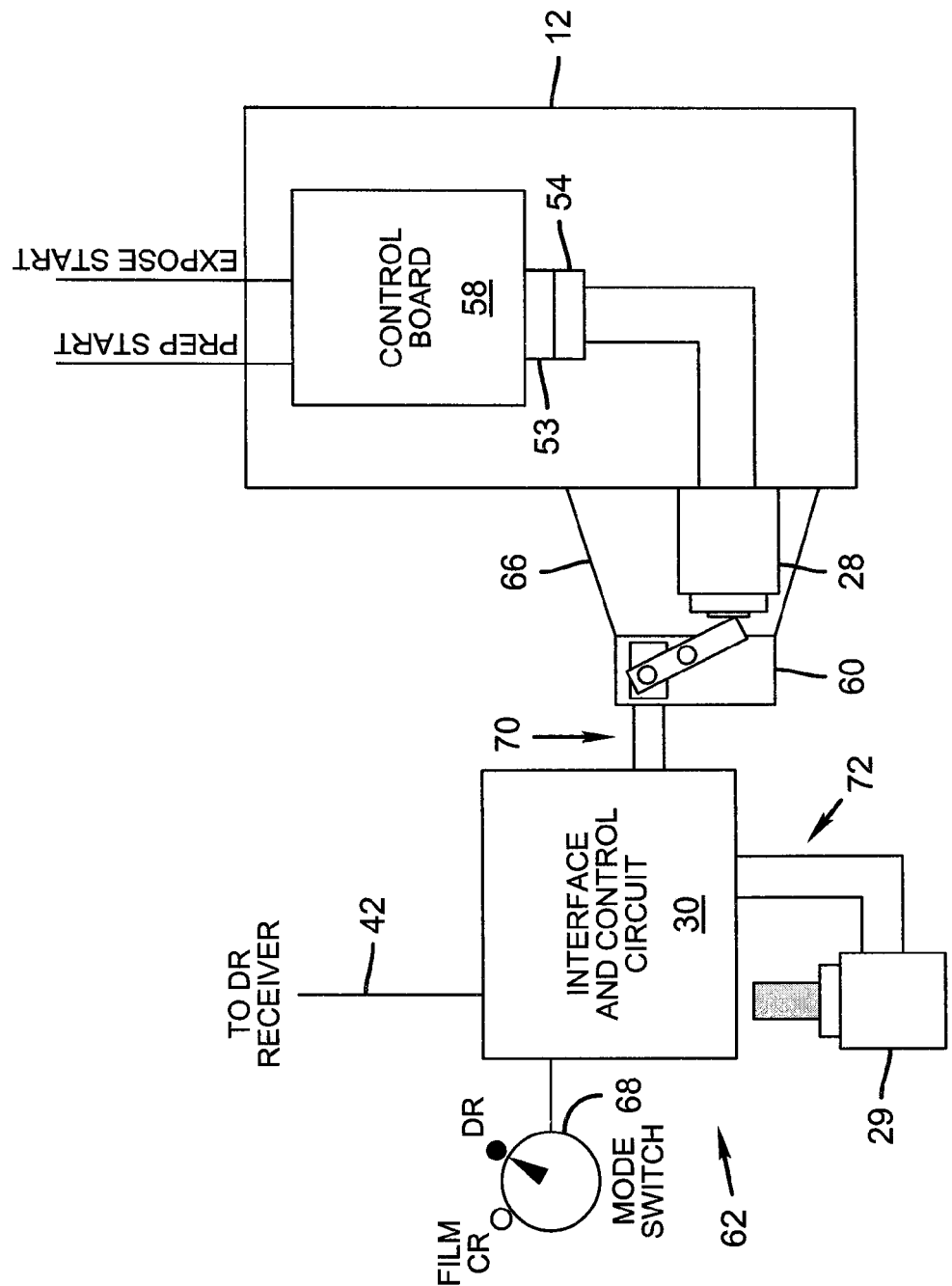
FIG. 5F is a schematic block diagram of an embodiment of a retrofit connection apparatus that mounts a separate switch controller on the operator control console for controlling a single two-position pushbutton.

The block diagram of FIG. 5F shows components in an embodiment of retrofit apparatus 62 using switch controller 60, mounted onto operator control console 12 and controlling the operation of pushbutton switch 28. Generator interface channel 70 connects to switch controller 60 and, based on the position of switch 29 as set by the operator, provides signals to actuators on switch controller 60 that urge pushbutton switch 28 into Prep or Expose positions, as described earlier. Switch 29 can be separately mounted or tethered, or can be mounted on switch controller 60, so that both operator interface channel 72 and generator interface channel 70 can follow the same basic path between switch controller 60 and interface and control circuit 30. No internal re-wiring is needed with this embodiment. Further details on configuration and operation of this device are given subsequently.

Figure 6:
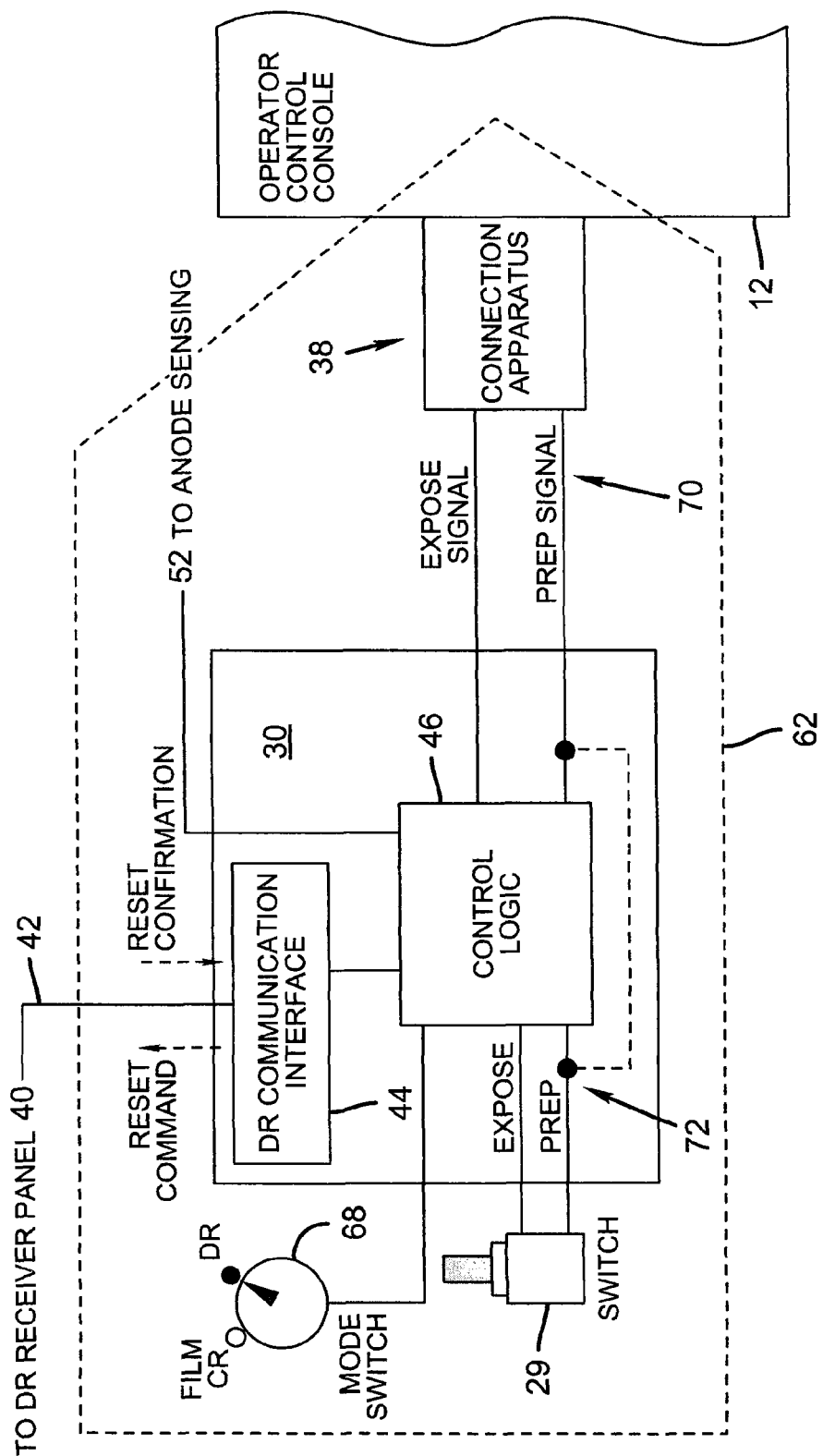
FIG. 6 is a schematic diagram showing the configuration, components, and signal handling for an interface and control circuit used in one embodiment of the present invention.

The schematic block diagram of FIG. 6 shows the functional components and signal connections of a retrofit apparatus 62 with interface and control circuit 30 in additional detail, with particular emphasis on its components as they relate to retrofit timing control. Components of retrofit apparatus 62 are generally outlined within the dashed-line boundaries. A control logic processor 46, which may be a microprocessor or other logic processing device having stored programmed instructions or may be implemented in hardware, runs the timing sequence for Prep and Exposure stages, as was described earlier with respect to FIG. 2. Prep and Expose signals from switch 29 are directed to control logic processor 46 for delay of the Expose signal timing, as described previously. In embodiments where the Prep signal only has the function of energizing the x-ray rotor, as shown in FIG. 2, the Prep signal may alternately bypass control logic processor 46, as indicated in a dotted line connection in FIG. 6.

Continuing with FIG. 6, a communication interface circuit 44 provides the needed interface for control and command data over receiver interface channel 42 with DR receiver panel 40. Communication interface circuit 44 is used to send the reset command, to receive confirmation of reset completion, and to terminate integration where sensor 56 or other device is used. Additional circuitry, not shown in FIG. 6, would be used for obtaining image data from DR receiver panel 40 through interface and control circuit 30 and for passing this image data on to imaging processor 32 and display 34, as shown earlier in FIGS. 3 and 4.

As shown in FIG. 6, connection apparatus 38, using an arrangement of components such as those shown in FIGS. 5B, 5C, 5D, 5E, and 5F provides the Prep and Expose signals from control logic on interface and control circuit 30 to operator control console 12 over generator interface channel 70. As described earlier, connection between connection apparatus 38 and operator control console 12 can be in any of a number of forms.

Figure 7A:
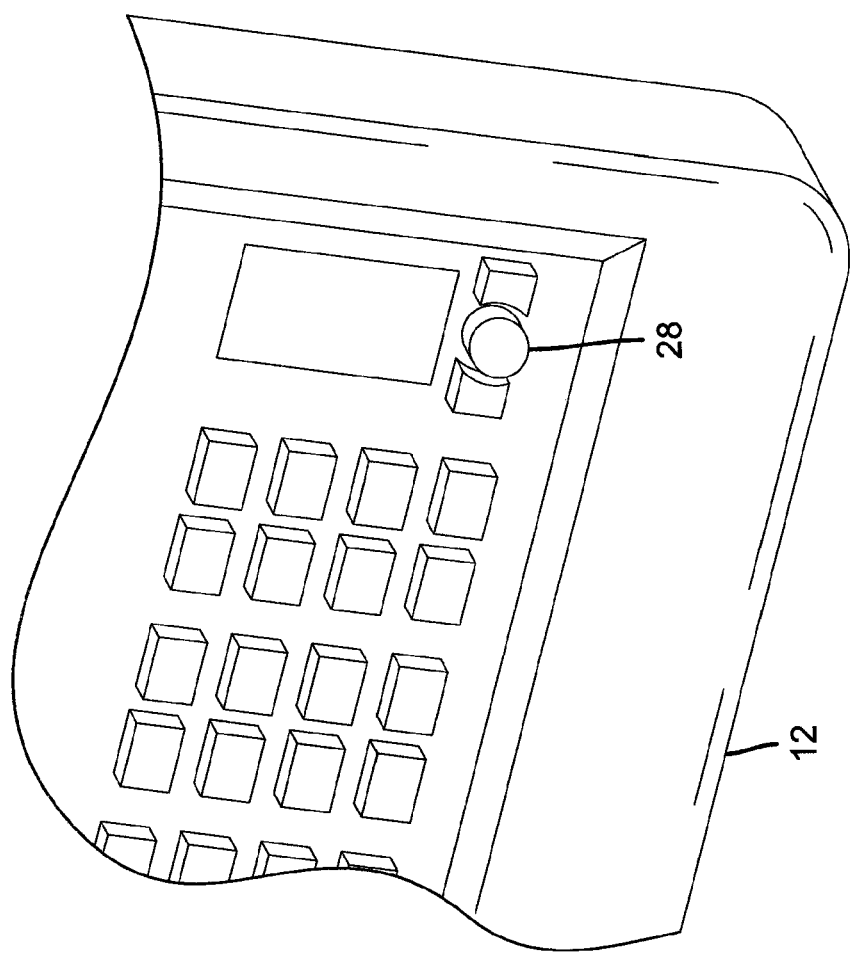
FIG. 7A is a perspective view showing the relative position of Prep/Expose pushbutton on a conventional control console.

The perspective view of FIG. 7A shows a conventional control console 12 having a single Prep/Exposure pushbutton control 28. The perspective view of FIG. 7B then shows an embodiment with switch controller 60 as a type of pushbutton control apparatus mounted onto operator control console 12. Switch controller 60 has a cover 66 and an optional access panel 74, in a retracted position in FIG. 7B, allowing selection of an alternate timing mode in one embodiment. A bypass switch 78 is accessible by sliding back access panel 74. Pressing bypass switch 78 enables the operator to bypass operation using the pushbutton control apparatus of switch controller 60, one option for specifying the mode when CR or film receivers are alternately used for imaging with the x-ray system.

Switch controller 60 mounts onto operator control console 12 in an appropriate manner. Mechanical fasteners can be used. In one embodiment, switch controller 60 is mounted onto operator control console 12 using adhesive material, such as a pressure-sensitive adhesive (PSA), for example.

Figure 7B:
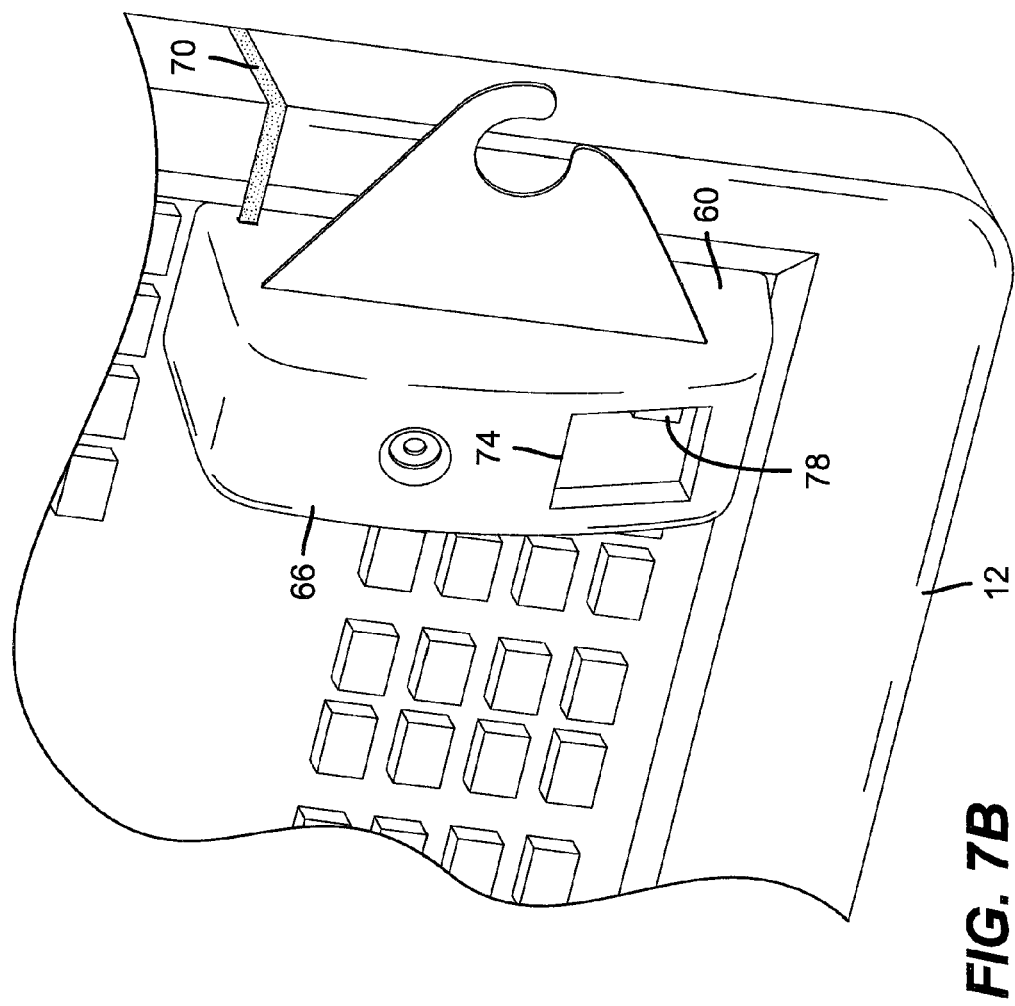
FIG. 7B is a perspective view of an operator control console for an x-ray imaging system with a retrofit using a pushbutton control apparatus in one embodiment of the present invention.

FIG. 8 is a perspective view of some of the inner components that are mounted within protective outer cover 66 of the pushbutton control apparatus, switch controller 60 of FIG. 7B in this embodiment, and shows their relation to the surface of operator control console 12. Based on operator use of switch 29 (as shown, for example, in FIGS. 5F and 6), the inner mechanism of switch controller 60 operates to urge pushbutton 28 to one of its operating positions by moving one end of a rocker arm 84, supported at a pivot 86. Actuators 80 and 82 cooperate to provide the needed force against pushbutton switch 28. In one embodiment, actuators 80 and 82 are solenoids. Alternate types of actuators 80 and 82 include motor driven shafts, lead screws, or cams, or other actuation devices driven magnetically, pneumatically, or using air pressure, for example.

Figure 9A:
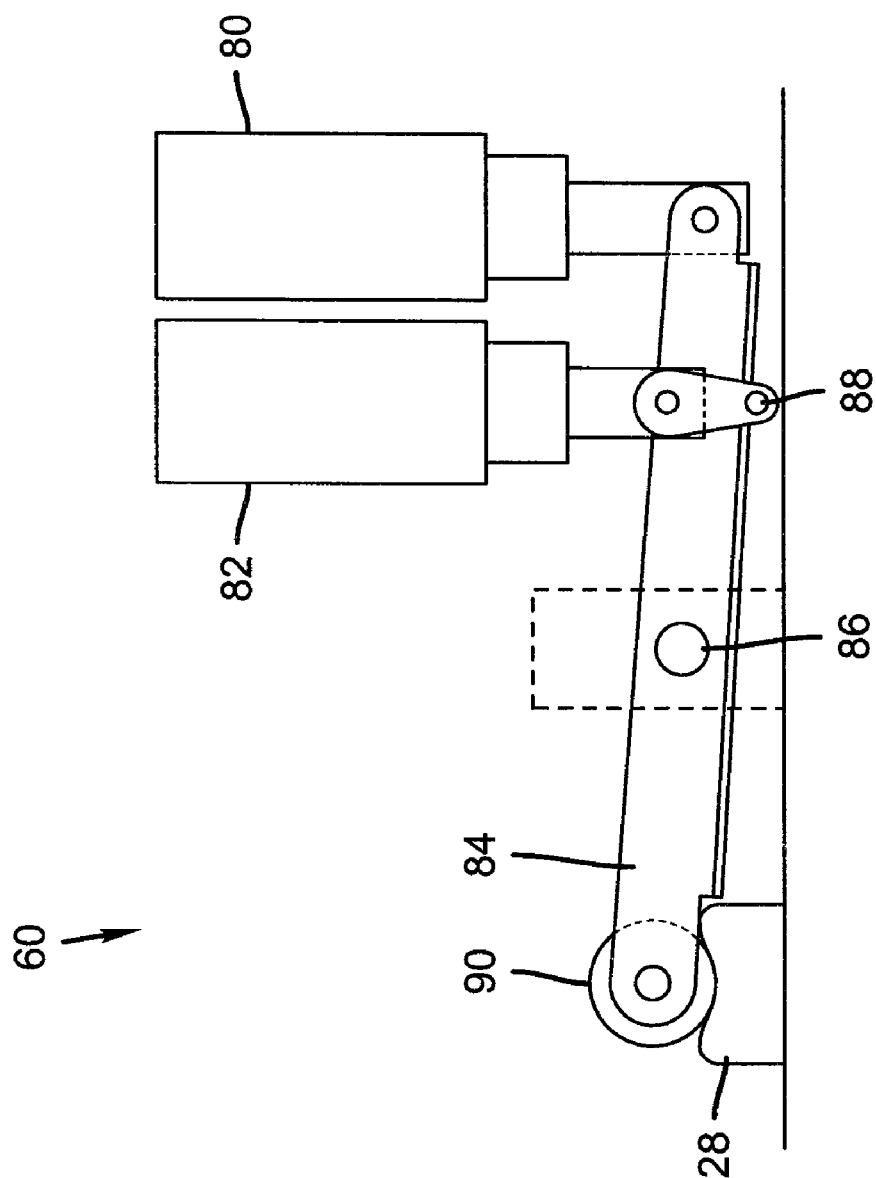
FIG. 9A is a schematic side view showing pushbutton control apparatus component position at rest in an idle state.
Figure 9B:
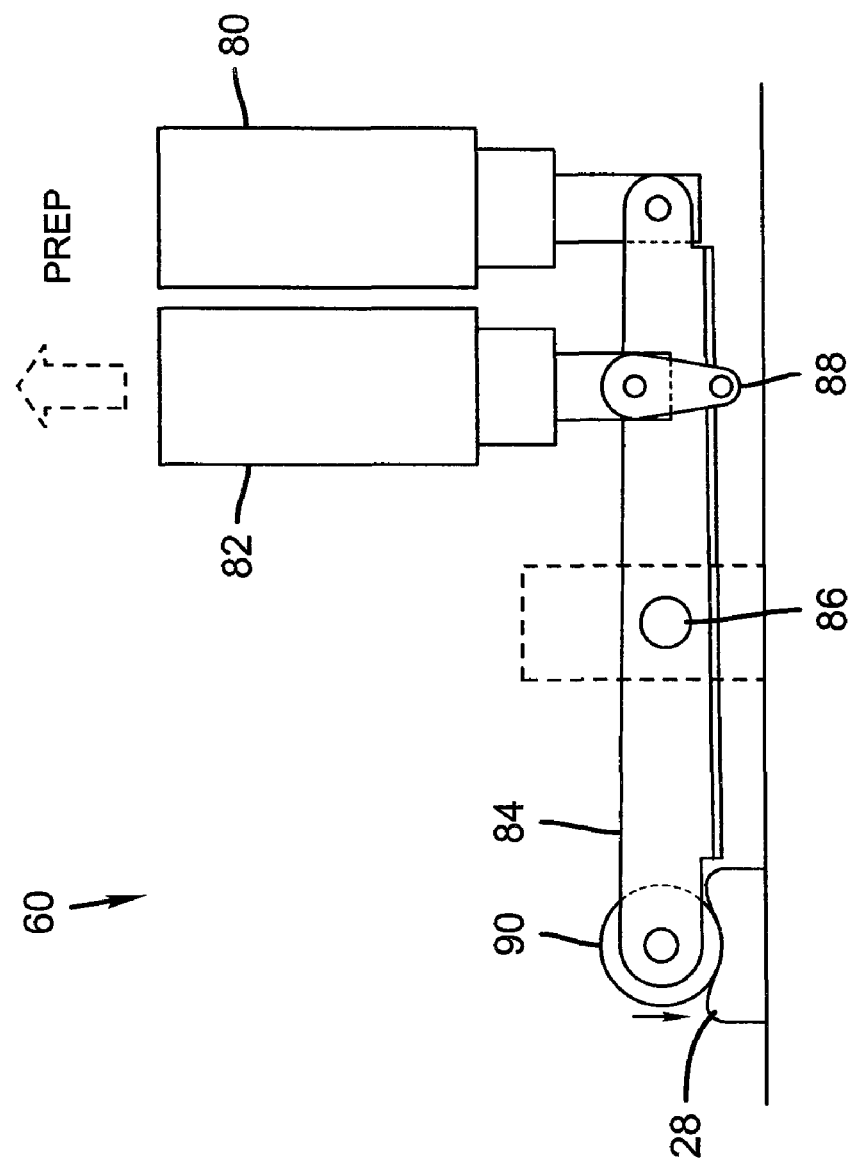
FIG. 9B is a schematic side view showing pushbutton control apparatus component position for actuation of the control panel pushbutton to a first setting.
Figure 9C:
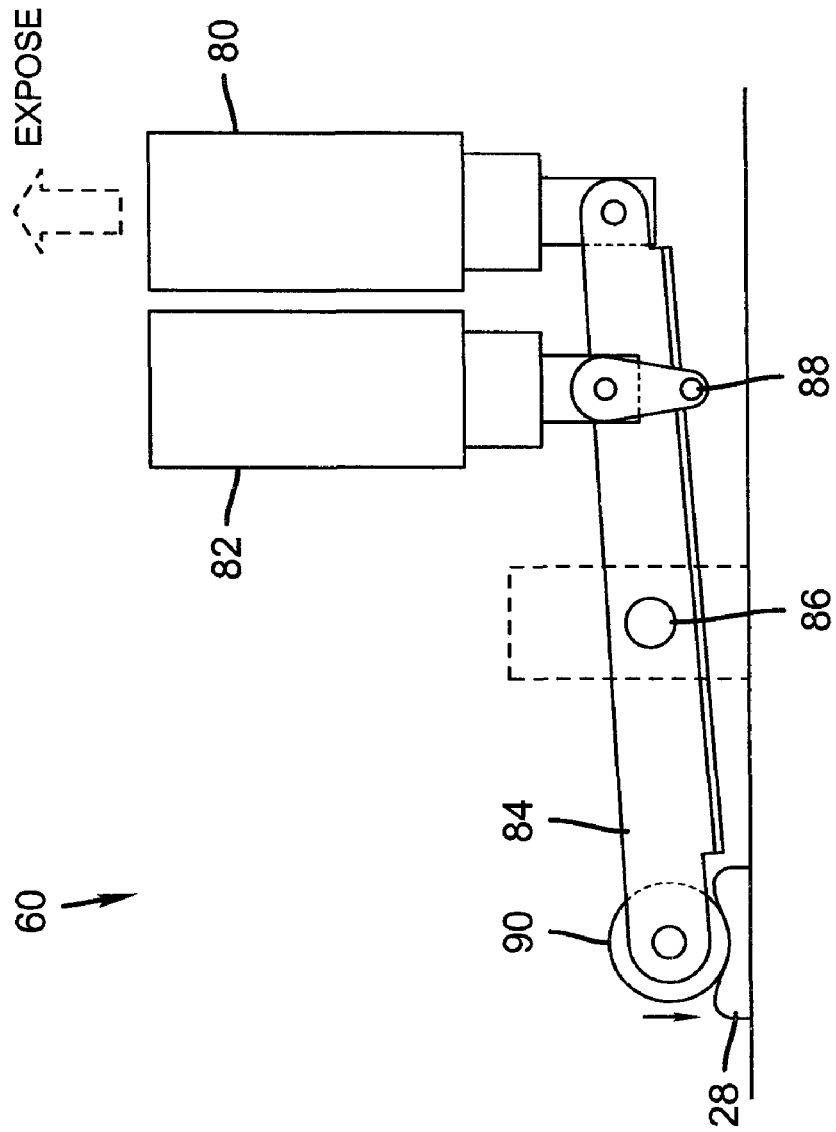
FIG. 9C is a schematic side view showing pushbutton control apparatus component position for actuation of the control panel pushbutton to a second setting.

The sequence of FIGS. 9A, 9B, and 9C shows the mechanical interaction of switch controller 60 components in the embodiment of FIG. 8, again with cover 66 removed. To give an idea of the relative amount of switch movement that is needed for pushbutton switch 28, exemplary values for the position of switch 28 are as follows in one typical embodiment:

| Selected State | Range of Switch 28 Movement |
|---|---|
| Idle | 0-1.3 mm |
| Prep | 1.5-2.6 mm |
| Expose | 5.5-6.7 mm |

FIG. 9A shows the pushbutton control apparatus at rest in an idle state. Pivot 86 is shown within an outlined rectangle to indicate that this point is held stationary by cover 66, which is removed for FIGS. 9A-C.

FIG. 9B is a schematic side view showing switch controller 60 component position for actuation of the control panel pushbutton to a first setting, the Prep setting for most x-ray systems. As shown by the dashed-outline arrow, actuator 82 is energized, pulling upward on the corresponding section of rocker arm 84. Actuator 80 is de-energized. A shaft 88 provides the upward support for moving rocker arm 84, using leverage from pivot 86. A wheel 90 at the end of rocker arm 84 provides a mechanical interface with reduced friction against pushbutton 28.

The schematic of FIG. 9C shows switch controller 60 component position for actuation of the control panel pushbutton to a second setting, the Expose setting. Here, actuator 80 is energized, pulling upward on the end of rocker arm 84. Actuator 82 remains energized, but is already at the end of its travel path. Rocker arm 84 lifts off of shaft 88 in this embodiment, as it is pivoted into this next position.

In one embodiment using solenoids, the use of two solenoids is advantaged over the use of a single actuator. It can be difficult to obtain a single solenoid capable of the full travel path for each signal position. Moreover, each solenoid has simple operation in the embodiment described with respect to FIGS. 9A-9C, having only fully energized or de-energized states.

Figure 10:
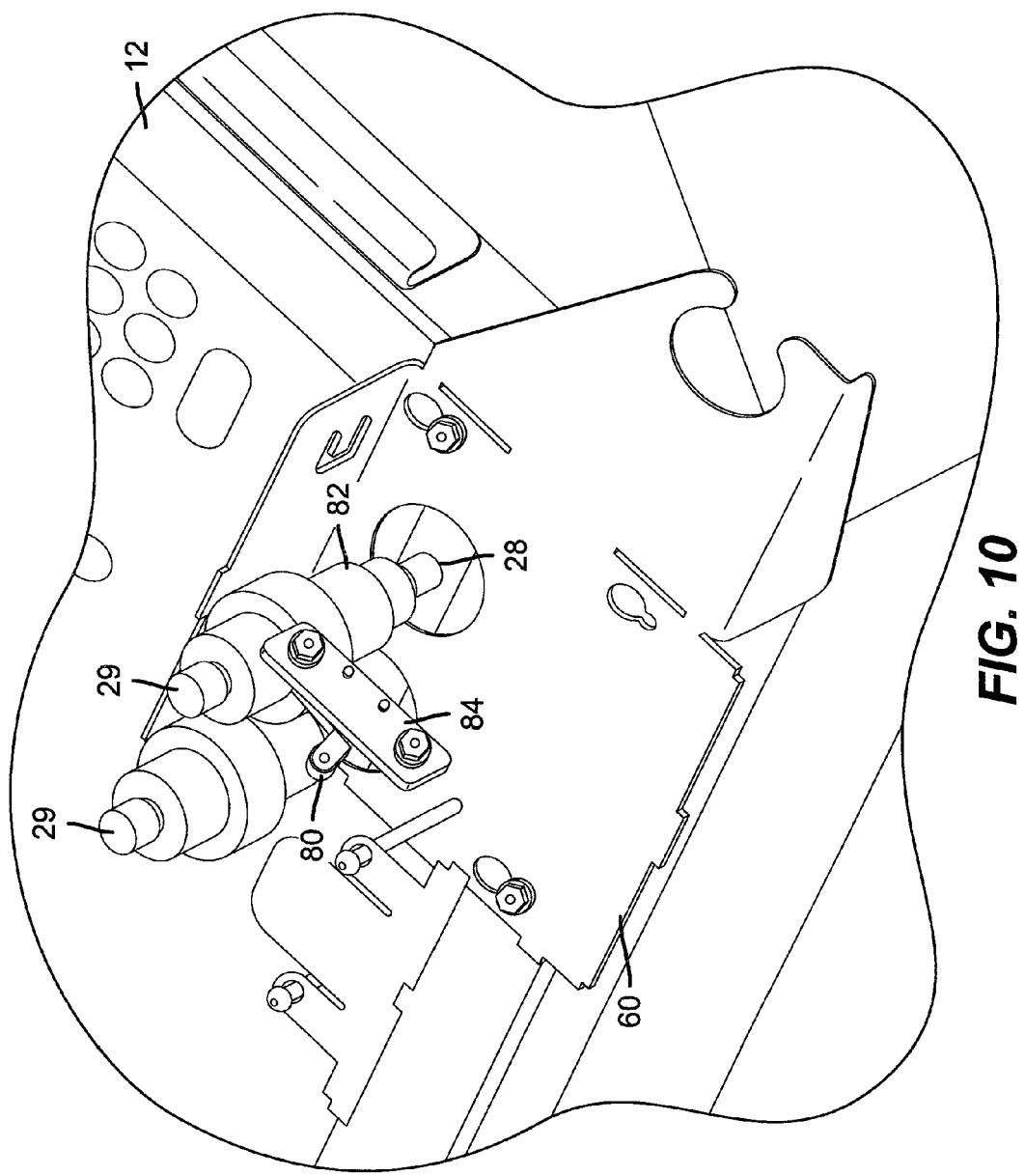
FIG. 10 is a perspective view of an alternate embodiment for a pushbutton control apparatus used with a control panel that has dual pushbuttons.

The alternate switch controller 60 embodiment of FIG. 10 shows an arrangement of internal components in which the pushbutton control apparatus of switch controller 60 mounts to a panel having separate Prep and Expose switches 28 as described earlier with reference to FIG. 5E, rather than the single-pushbutton embodiment for the devices shown in FIGS. 7B-9C. Switch controller 60 again has two actuators 80 and 82, one for controlling each of the two switches 28. Pressing the Prep switch 29, on the left side in the embodiment of FIG. 10, energizes actuator 80 for pressing Prep switch 28 on control console 12. Pressing the Expose switch 29 on the right side in this embodiment sends a signal to control logic processor 46 in interface and control circuit 30 (FIG. 5E). Drive current that energizes actuator 82 for pressing the Expose switch is transmitted through control logic processor 46. The Expose signal then goes to control board 58.

The invention has been described in detail with particular reference to a presently preferred embodiment, but it will be understood that variations and modifications can be effected within the spirit and scope of the invention. For example, various types of cable connections can be used for forming each interface channel, in this case, providing Prep and Expose signals from interface and control circuit 30 over generator interface channel 70. Wired or wireless communication could be used from interface and control circuit 30 over any individual interface channel 42, 70, and 72.

The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST 10. x-ray imaging system
12. Operator control console
14. Control room
16. Film-based or computed radiography cassette
18. Patient
20. Radiation room
22. x-ray generator
24. x-ray tube
28. Operator control switch
29. Operator control switch
30. Interface and control circuit
32. Imaging processor
34. Display
38. Connection apparatus
40. DR receiver panel
42. DR receiver interface channel
44. Communication interface circuit
46. Control logic processor
48. Transceiver connected to interface and control circuit 30
50. Retrofitted imaging system
52. Transceiver connected to DR receiver panel 40
53, 53', 54, 55. Connector
56. Sensor of anode current in 24
58. Control board
60. Switch controller
62. Retrofit apparatus
66. Cover
68. Mode selector
70. Generator interface channel
72. Operator interface channel
74. Access panel
78. Bypass switch
80, 82. Actuator
84. Rocker arm
86. Pivot
88. Shaft
90. Wheel
D1 Delay period after Expose state of 28
D2 Reset period of DR receiver panel 40
D3 Period of anode current for x-ray generator 22

What is claimed is:

1. A method for obtaining an image by using a digital radiography receiver in an x-ray imaging system of a type configured for film or computed radiography, the method comprising:
    providing a retrofit connection apparatus that adapts the x-ray imaging system for use with the digital radiography receiver by:
    forming a receiver interface channel for communicating signals to and from the digital radiography receiver;
    forming an operator interface channel for routing at least an input expose signal from an operator control to the retrofit connection apparatus; and
    forming a generator interface channel for transmitting at least an output expose signal from the retrofit connection apparatus to an x-ray generator of the x-ray imaging system;
    in response to the input expose signal routed over the operator interface channel, transmitting the output expose signal to the x-ray generator over the generator interface channel;
    providing the retrofit connection apparatus a first mode for operating the x-ray imaging system with the digital radiography receiver; and
    providing the retrofit connection apparatus a second mode for operating the x-ray imaging system with an x-ray film cassette or a computed radiography cassette, wherein the x-ray film cassette and the computer radiography cassette are removed from the x-ray imaging system to output an image and the digital radiography receiver is not removed from the x-ray imaging system to output an image.

2. The method of claim 1 wherein forming an operator interface channel comprises providing a hand-held switch.

3. The method of claim 1 further comprising, in response to the input expose signal, initiating image signal integration at the digital radiography receiver before transmitting the output expose signal.

4. The method of claim 1 further comprising providing a mode selector that selects an alternate timing sequence wherein the input expose signal is directly provided as the output expose signal.

5. An apparatus for x-ray imaging comprising:
    a receiver interface channel to communicate with a digital radiography receiver,
    a generator interface channel to communicate with an x-ray generator of an x-ray imaging system;
    an interface component installed as a retrofit to the x-ray imaging system, the interface component comprising:
    a mode selector to select at least a first mode setting for image capture using a digital radiography receiver and a second mode setting for image capture using a removable film or computed radiography cassette;
    an operator interface channel to communicate with an operator control for receiving at least a first, preparation signal and a second, expose signal from an operator; and
    a programmed control logic processor that, when the first mode setting is selected, responds to such a second, expose signal from the operator interface channel by transmitting an exposure signal for the x-ray generator of such a system over the generator interface channel, wherein the operator control is a single manually operated actuator used in both the first mode setting and the second mode setting to generate the first preparation signal and the second expose signal.

6. The method of claim 1 wherein forming a receiver interface channel further comprises providing a wireless communication link between the retrofit connection apparatus and the digital radiography receiver.

7. The method of claim 1 wherein forming an operator interface channel comprises disconnecting at least one control switch from a first connector comprised in the x-ray imaging system and connecting the at least one control switch to a second connector comprised in the retrofit connection apparatus.

8. The method of claim 1 wherein forming an operator interface channel comprises mounting a device that covers at least one front panel switch of the x-ray imaging system.

9. The method of claim 1 further comprising receiving an acknowledgement of reset from the digital radiography receiver before transmitting the output expose signal.

10. The method of claim 1, further comprising providing the retrofit connection apparatus with a variable preset delay timer set according to operations of an x-ray source of the x-ray imaging system.

11. The method of claim 1, wherein the variable preset delay timer is set according to x-ray tube rotor spin up or anode current generation at the x-ray imaging system.

12. The method of claim 6 further comprising sensing an x-ray anode current level at least during image exposure, and terminating signal integration on the digital radiography receiver according to the sensed x-ray anode current level.

13. The apparatus of claim 5 wherein the receiver interface channel comprises a wireless communication link for use between the interface component and such a digital radiography receiver, and wherein the mode selector provides an instruction to the control logic processor.

14. The apparatus of claim 5 wherein the interface component further comprises a sensor for x-ray anode current level of such a system.

15. The apparatus of claim 5 wherein the interface component further comprises a sensor for providing a signal indicative of x-ray emission according to a sensed electrical current level, wherein signal integration is terminated based on the signal indicative of x-ray emission.

16. The apparatus of claim 11 wherein the generator interface channel further comprises a switch controller for covering at least a first switch on a control panel of such a system and for controlling the setting of at least the first switch according to a setting of a second switch by an operator, wherein the second switch is mounted on the switch controller, and wherein the switch controller further comprises at least one actuator that is controlled by a signal from the interface component on the generator interface channel.

17. A method for obtaining an image by using a digital radiography receiver in an x-ray imaging system of a type configured for film or computed radiography, the method comprising:
   providing a retrofit connection apparatus to operate the x-ray imaging system in a first mode for use with the digital radiography receiver by:
   forming a receiver interface channel for communicating signals to and from the digital radiography receiver;
   forming an operator interface channel for routing at least an input expose signal from an operator control to the retrofit connection apparatus; and
   forming a generator interface channel for transmitting at least an output expose signal from the retrofit connection apparatus to an x-ray generator of the x-ray imaging system;
   in response to the input expose signal routed over the operator interface channel, transmitting the output expose signal to the x-ray generator over the generator interface channel; and
   providing the retrofit connection apparatus a second mode to operate the x-ray imaging system for use with a film receiver or a computed radiography receiver,
   wherein the retrofit connection apparatus does not change an interior of the x-ray imaging system.

18. The method of claim 17, wherein the x-ray imaging system uses the same single manual actuator as an operator interface in the first mode and the second mode, wherein the single manual actuator is a press button or a switch.

19. The method of claim 17, wherein the retrofit connection apparatus does not change an exterior of the x-ray imaging system.

20. A method for obtaining an image by using a digital radiography receiver in an x-ray imaging system of a type configured for film or computed radiography, the method comprising:
   providing a retrofit connection apparatus that adapts the x-ray imaging system for use with the digital radiography receiver by:
   forming a receiver interface channel for communicating signals to and from the digital radiography receiver;
   forming an operator interface channel for routing at least an input expose signal from an operator control to the retrofit connection apparatus; and
   forming a generator interface channel for transmitting at least an output expose signal from the retrofit connection apparatus to an x-ray generator of the x-ray imaging system;
   in response to the input expose signal routed over the operator interface channel, transmitting the output expose signal to the x-ray generator over the generator interface channel;
   providing the retrofit connection apparatus a first mode for operating the x-ray imaging system with the digital radiography receiver;
   providing the retrofit connection apparatus a second mode for operating the x-ray imaging system with an x-ray film cassette or a computed radiography cassette, wherein the x-ray film cassette and the computer radiography cassette are removed from the x-ray imaging system to output an image and the digital radiography receiver is not removed from the x-ray imaging system to output an image; and
   sensing an x-ray emission at least during image exposure, and terminating signal integration on the digital radiography receiver according to the sensed x-ray emission.

* * * * *